United States Patent [19]
Rubin

[11] Patent Number: 5,059,603
[45] Date of Patent: Oct. 22, 1991

[54] METHOD AND COMPOSITION FOR TREATING IMPOTENCE

[75] Inventor: David Rubin, San Diego, Calif.

[73] Assignee: Centuries Laboratories, Inc., Port Washington, N.Y.

[21] Appl. No.: 364,289

[22] Filed: Jun. 12, 1989

[51] Int. Cl.$^5$ .............................................. A61K 31/52
[52] U.S. Cl. .................................. 514/264; 514/742; 514/947
[58] Field of Search ............... 514/264, 367, 415, 947, 514/647, 742, 248; 424/608

[56] References Cited

U.S. PATENT DOCUMENTS

| | | | |
|---|---|---|---|
| 2,550,398 | 4/1951 | Barol . | |
| 3,483,870 | 12/1969 | Coover, Jr. et al. . | |
| 3,740,420 | 6/1973 | Herschler et al. . | |
| 3,896,238 | 7/1975 | Smith | 424/358 |
| 3,953,599 | 5/1976 | MacMillan et al. | 424/265 |
| 4,127,118 | 11/1978 | Latorre | 128/79 |
| 4,285,967 | 8/1981 | Gubernick et al. | 424/289 |
| 4,444,762 | 4/1984 | Rajadhyaksha | 424/180 |
| 4,557,934 | 12/1985 | Cooper | 514/399 X |
| 4,575,515 | 3/1986 | Sandborn | 514/708 |
| 4,743,588 | 5/1988 | Mirejovsky et al. | 514/24 |
| 4,746,675 | 5/1988 | Makino et al. | 514/423 |
| 4,764,379 | 8/1988 | Sanders et al. | 424/449 |
| 4,764,381 | 8/1988 | Bodor et al. | 424/449 |
| 4,789,667 | 12/1988 | Makino et al. | 514/161 |
| 4,795,756 | 1/1989 | Oxford et al. | 514/415 |
| 4,801,586 | 1/1989 | Minaskanian et al. | 514/212 |
| 4,801,587 | 1/1989 | Voss et al. | 514/248 |
| 4,808,414 | 2/1989 | Peck et al. | 424/449 |

OTHER PUBLICATIONS

Morales et al., *Urologic Clinics of North America* 15: (1) 87–93, 1988.
Moshikov, Chemical Abstracts vol. 52, 1958, Abstract 5637h.
Ilarionov et al., Chem. TBS. vol. 111, No. 11 entry #89683f (1989).
Barbanti et al., Urol. Res. vol. 16 (4) pp. 299–302. (1988).
Kiely et al., British J. Vrol. vol. 59 (4) pp. 334–339 (1987).

Primary Examiner—Mukund J. Shah
Assistant Examiner—E. C. Ward
Attorney, Agent, or Firm—Browdy and Neimark

[57] ABSTRACT

A composition for treating impotence contains a vasodilator, a vasoconstrictor, and a penetration enhancing ingredient in a pharmaceutically acceptable carrier for topical application. The composition is applied topically to treat impotence.

2 Claims, No Drawings

METHOD AND COMPOSITION FOR TREATING IMPOTENCE

FIELD OF THE INVENTION

The present invention relates to a composition and method for treating impotence.

BACKGROUND OF THE INVENTION

Impotence, or lack of a man's ability to have sexual intercourse, is often the subject of parlor humor, but millions of men suffer from this condition, regardless of age, Impotence is generally characterized by an inability to maintain a penile erection.

Causes of impotence are numerous. It may be atonic, due to paralysis of the motor nerves (nervi erigentes) without any evidence of lesions to the central nervous system. Conversely, it could be paretic as a results of a lesion in the central nervous system, particularly the spinal cord. Alternatively, it could be psychic, and dependent on a mental problem or instability. Finally, it could be symptomatic, due to some other disorder, such as injury to nerves in the perineal region, by virtue of which the sensory portion of the erection reflex is blocked out.

Whether the impotence is absolute, involving all sexual modalities, total, affecting all sexual function, though not necessarily libido, or partial, affecting the rigidity or duration of the erection, or whether the cause of impotence is organic, due to structural changes, disease, or some demonstrable functional impairment anywhere in the sexual system, psychogenic, due to old age or sexual satiation, the result is the same: at least partial inability to engage in sexual activity due to the lack of an adequate erection.

Impotence may be defined more fully, however, as the inability to develop or sustain an erection of the penis sufficient to conclude coitus or orgasm and ejaculation to the male's own satisfaction. Impotence treatment methods are generally, however, concerned with the erection aspect, and not ejaculatory impotence, which is relatively rare.

The body of the penis is surrounded by a cornified layer of skin. Blood is supplied through the dorsal artery and removed through the dorsal vein. The urethra is surrounded by a fibrous compartment known as the corpus songiosum, which permits urination and provides a path for semen during ejaculation.

The corpora cavernosa form the chief part of the body of the penis, and at their rear portion they form the crura where the penis is firmly connected to the pelvis and ischium. The corpora cavernosa are surrounded by a fibrous sheath having exterior and interior portions respectively. The portion of the corpora cavernosa within the fibrous sheath consists of a sponge-like tissue of arveolar spaces freely communicating with each other and filled with venous blood. This space may be thought of as a large cavernous vein. The arteries bringing blood to these spaces are the arteries of corpora cavernosa and branches from the dorsal artery, which perforate the fibrous sheath along the upper surface thereof.

Under the proper stimulus, the penis becomes erect when the corpora cavernosa become widely dilated with arterial blood, thereby causing these tissues to become less flaccid. At the extreme side of the corpus cavernosum, tiny veins are connected to nerve endings, and, upon the proper stimulus, the veins assume a position so as to block outflow of blood from the corpus cavernosum. This mechanism is psychologically controlled.

The turgor phenomenon is generally caused by an action of the autonomic nervous system. The autonomic nervous system consists of two divisions, the sympathetic nervous system and the parasympathetic nervous system. In a healthy individual, activity by one of the two autonomic nervous system results in a physiological effect opposite to that of the activity of the other system. An autonomically-controlled physiological state is determined, at any time, by the relative degree of activity of the two systems.

The autonomic system controls the blood flow in the penis by means of peripheral nerves attached to the arterial vessels in and around the corpora cavernosa. During normal physiological activity, the sympathetic nerves maintain these arteries in a constricted state. As the man becomes aroused, his parasympathetic system releases certain chemicals, principally catecholamines such as norepinephrine and epinephrine, which inhibit the action of the sympathetic nerves resulting in relaxation of the smooth muscles surrounding the arteries and thus dilation thereof.

In the case of neurological problems, the nerves cannot convey the proper stimulus to either the arteries or the veins, This is the case with diabetics or patients with problems of the peripheral nervous system. In the case of a patient afflicted with arteriosclerosis, which often accompanies aging, the arteries cannot carry sufficient blood to the corpus cavernosum because of obstruction.

The most widely used therapy for treating impotence has been the implantation of penile prostheses. The simplification of the surgical technique, the obvious and rapid solution of the difficulties for intromission, and the popular appeal of prostheses all inhibited the search for pharmacologic intervention. However, recently, a great interest has developed in the use of a variety of agents for improving both libido and the quality of erections.

Many blood constrictive devices have also been proposed for producing and enhancing an erection. Typically, these are adjustable, tourniquet-like rubber band devices which are designed to fit tightly around the shaft of the penis and thereby restrict the flow the blood from the penis through the surface veins, as well as the deeper dorsal vein, to prolong an erection. There have been numerous attempts to solve this problem, but all exhibit various disadvantages to the user, and sometimes to the female partner, such as extreme discomfort during intercourse, to the extent that users might not achieve the desired usefulness as frequently as desired and to the extent preferred. All of the external devices previously proposed have the psychological disadvantages of being an impediment to actual intercourse, and the operational disadvantage that their duration of effectiveness is relatively short.

Impotence associated with androgen deficiency has long been thought by certain medical factions to be treatable by the administration of male hormones via synthetic preparations such as methyl testosterone and various esters, as well as a number of testosteroneaphrodisiac compositions. The relationship between testosterone levels and impotence has not been firmly established. However, the administration of exogenous hormones has several pharmacologic disadvantages. For example, methyl testosterone must be taken subcutaneously or bucally, and may cause severe toxic effects such as cholestatic jaundice. Parenterally administered testosterone esters, while less toxic and more certainly absorbed than methyl testosterone, have the drawbacks of intramuscular administration including additional pain, lack of complete absorption, and risk of deep and widespread infection. Additionally, long-term administration of these synthetic compounds may inhibit endogenous testosterone formation and spermatogenesis by suppressing pituitary gonadotropin, resulting in glandular tissue atrophy because of disuse.

Because of the uncertainty and the problems involved in the administration of testosterone in the treatment of impotence, there have been numerous nonandrogen attempts to treat the impotence problem, including treatments with yohimbine, damiana, ginseng, levodopa, hydergine, clomiphene, phosphorous, strychnine, and cantharides. Other drugs tested for treating impotence include bromocriptine, nitroglycerin, zinc, oxytocin, and lutenizing hormone-releasing hormone. These are generally administered orally with varying degrees of success, some with significant side effects.

Intracorporeal injections of papaverine have been investigated for some time, and this has become one of the more commonly used of the various pharmacologic agents. Alternatively, as disclosed by Latorre in U.S. Pat. No. 4,127,118, nonsteroidal agents, including an appropriate vasodilator, can be injected into the corpus cavernosa to cause an erection. Among the vasodilators that can be used are sympathomimetic amines or adrenergic blocking agents, or other agents within the histamine and epinephrine groups. The most obvious drawback to this type of treatment is the need for an infection whenever an erection is desirable.

Topical agents have also been proposed to induce an erection, such as disclosed in Voss et al., U.S. Pat. No. 4,801,587. The ointment disclosed therein comprises a vasodilator or alpha-blocker in an ointment base, along with a carrier. However, in this case, the ointment only includes an agent to dilate the arterial vessels, and there is nothing to constrict the veins to retain the blood in the corpora cavernosa.

Nitroglycerin paste has been widely used in the treatment of angina. Morales et al., in *Urologic Clinics of North America* 15:(1) 87-93, 1988, disclose the results of a double-blind, controlled randomized trial of nitroglycerin paste versus placebo paste under strictly controlled laboratory conditions. This study demonstrated that nitroglycerin transcutaneously administered enhances the quality of erectile episodes in the presence of an erotic stimulus and under laboratory conditions. An important consideration is the effect of the drug on the sexual partner, since nitroglycerin is readily absorbed by the vaginal mucosa. One case of secondary headache in the sexual partner of an individual who used nitroglycerin on his penis has been reported.

SUMMARY OF THE INVENTION

It is an object of the present invention to overcome the above-noted deficiencies in the prior art.

It is another object of the present invention to provide a composition for treating impotence.

It is a further object of the present invention to provide a method for treating impotence.

It is still another object of the present invention to provide an improved method of treating impotence without afflicting the partner with secondary headaches.

According to the present invention, impotence is treated by transcutaneous administration of a combination of a vasodilator and a vasoconstrictor in a carrier including an agent to assist absorption of the active ingredients through the skin around the penis. The vasodilator and vasoconstrictor are chosen so that the vasodilator acts more quickly than the vasoconstrictor. When the vasodilator enters the corpora cavernosa within the penis, it causes dilation of the corpora, resulting in an erection. Then, when the later-acting vasoconstrictor enters the corpora cavernosa, it causes the veins to constrict and thus retain the blood in the erect penis to enhance the erection. A topically applied antiinflammatory agent can be used to prevent local irritation of the skin.

The composition of the present invention is topically applied, and thus can be incorporated in any suitable carrier. The active ingredients can be present in the composition in amounts ranging from approximately 0.05 to 5.0% by weight of vasodilator, from about 0.05 to about 5.0% by weight of vasoconstrictor, and from about 50 to about 90% of penetration-enhancing agent. Any carrier suitable for topical administration can be used. Where an antiinflammatory agent is used, it can be present in amounts ranging from about 0.05 to about 1% by weight.

DETAILED DESCRIPTION OF THE INVENTION

Impotence can be treated by topical application of a composition containing a vasodilator, a later-acting vasoconstrictor, and an absorption enhancing agent in a pharmaceutically acceptable carrier. The vasodilator provides almost immediate blood vessel congestion. The vasoconstrictor is absorbed less quickly, perhaps three to four minutes later, and serves to retain the blood in place. An anti-inflammatory agent can be used to prevent or minimize local irritation of the skin.

While any vasodilator that adequately opens the blood vessels will suffice for the treatment of impotence according to the present invention, the preferred drugs are those which produce vasodilation by direct action on the arteries themselves. This includes vasodilators or alpha-blockers which can be administered topically, including nitroglycerin, papaverine (6,7-dimethoxyl-1-veratrylisoquinoline), hydralzaine, sodium nitroprusside, phenoxybenzamine, isoxaprine hydrochloride, nylidrin hydrochloride, tolazoline hydrochloride, nicotinyl alcohol, and phentolamine. A single application should contain between one and 5 milligrams of the vasodilator.

Of these drugs, nitroglycerin is currently extensively used in treatment of angina pectoris, and is a well known vasodilator. Nylidrin is a sympatomimetric amine, and exerts a pharmacologic action on skeletal muscle blood vessels similar to that of epinephrine. Nylidrin increases blood flow by a direct vasodilating action on the arteries, and has no significant effect on pulse rate or blood pressure.

Isoxsuprine hydrochloride increases blood flow by direct relaxation of the vascular musculature. This drug also has a slight adrenergic blocking action, but this is not essential to its vasodilating effect. This drug is conventionally used in treating certain obliterative vascular diseases such as arteriosclerosis and andarteritis obliterans, and in vasospastic diseases.

Tolazoline is an adrenergic blocking agent related structurally to both histamine (a vasodilator) and epinephrine. Tolazoline also acts by a direct dilating effect on the walls of blood vessels, and provides a sympathetic block, probably at the terminations of sympathetic nerves. It also has an anti-adrenergic effect which blocks the vasoconstrictive action of epinephrine and levarterenol. While tolazoline traditionally is administered orally in the treatment of various peripheral vascular disorders, the preferred dosage for use topically in the present invention is from about 10 to about 25 milligrams.

Nicotinyl alcohol is converted to nicotinic acid in the body to produce peripheral vasodilation, thereby increasing blood flow to extremities when administered orally. The preferred topical dosage for use in treating impotence according to the present invention ranges from about 10 to about 25 milligrams. A disadvantage of this drug is that side effects such as flushing of the face and gastrointestinal disturbances may result, particularly at high dosage. However, side effects should generally be minimal with the dosage of the present invention.

The vasoconstrictors which can be used in the present invention include those vasoconstrictors which can be administered topically, including caffeine, a well known ingredient in coffee and tea. A variety of other vasoconstrictors can be used in the present invention, including 3-(2-aminoethyl)indole derivatives, described more fully in U.S. Pat. No. 4,795,756, to Oxford et al., and hereby incorporated by reference. These compounds have traditionally been used for treatment of migraine headaches, and in the method of the present invention are administered in dosages of from about 0.1 to 00 mg. Another group of vasoconstrictors that can be used in the present invention is the adrenergic agents including pressor amines of the β-phenylethylamine type, including epinephrine, also known as adrenaline. Examples of other compounds of this type are given in U.S. Pat. No. 3,483,870, to Coover, Jr. et al., which patent is hereby incorporated by reference. These compounds are generally used in amounts ranging from about 1 to about 200 mg per dose in the present invention, and are generally chosen so that they act somewhat later than the vasodilators with which they are combined in the compositions according to the present invention.

The absorption or penetration enhancers most preferably used in the compositions according to the present invention are the aliphatic sulfoxides of the formula RSOR', wherein R is an alkyl, substituted alkyl, alkenyl, or hetero group containing up to 12 carbon atoms, and R' is a low molecular weight alkyl or hydroxy-substituted alkyl group. The most commonly used of these, and the compound preferably used in the present invention, is dimethylsulfoxide. The compositions according to the present invention must contain at least about 50% dimethylsulfoxide in order to achieve efficient, cient, practical penetration of the skin barrier. Lower concentrations may thus result in less than the desired effect. On the other hand, with very high concentrations of dimethylsulfoxide, such as substantially above about 95%, the undesired side effects of local skin irritation and dehydration, erythema, and urticaria increase markedly, while no substantial increased benefit is obtained, and the rate of penetration of the active ingredients may actually be lessened. In the present invention, for dermal application, diluting the dimethylsulfoxide with an appropriate diluent can minimize these side effects and enhance acceptability of the compositions.

Therefore, for a highly advantageous administration of dimethyl sulfoxide to the intact skin, because of the unusual penetration properties of the dimethylsulfoxide, compositions containing from about 50% to about 90% dimethylsulfoxide with a pharmaceutically acceptable diluent have been found to be uniquely suitable and desirable. Dimethylsulfoxide-glycerin solutions of 10% to 40% glycerin content are quite advantageous to minimize skin irritation both from the dilution of the dimethyl sulfoxide and the emollient effects of the glycerin, which tends to sooth the irritation and skin dryness which may be caused by the dimethyl sulfoxide.

A number of other penetration enhancers can be used in the compositions according to the present invention. Among these are optically active or inactive pyroglutamates of the following formula

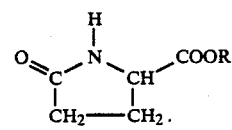

wherein R is a linear, branched, or cyclic alkyl or alkenyl group having from 10 to 14 carbon atoms. These pyroglutamic esters are contained in large amounts in human skin, and are among the natural moisturizing factors in skin.

Among other penetration enhancers that can be used in compositions according to the present invention are glycerol monolaurate, dimethylacetamide, propylene glycol, or other organic esters such as diisopropyl adipate or isopropyl myristate. Additional penetration enhancers for use in compositions according to the present invention include surfactants such as sodium laurylsulfate and polyoxyethylene-2-sorbitan monolaurate. U Another effective penetration enhancer for use in the present invention is 2-ethyl-1,3-hexanediol either alone or in combination with oleic acid.

Another group of compounds which are useful in the present invention are penetration enhancers of the formula

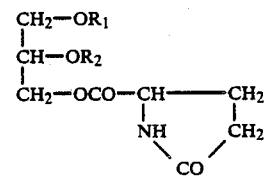

wherein $R_1$ and $R_2$ are identical or different and each represents H, a $C_{1-25}$ alkyl, $C_{2-\text{alkenyl}}$, a ($C_{1-24}$ alkyl) carbonyl or a ($C_{2-24}$ alkenyl) carbonyl, provided that $R_1$ and $R_2$ are not H at the same time, or $R_1$ and $R_2$, taken together, may form a group of the following formula:

in which $R_3$ and $R_4$ are identical or different and each represents H, $C_{1-24}$ alkyl, or $C_{1-24}$ alkenyl.

Another group of penetration enhancing agents includes amides of heterocyclic amines of the following structural formula:

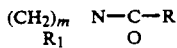

wherein m is from 4 to 9;

$R_1$ is hydrogen or an alkyl group having from 1 to 8 carbon atoms; and

R is a straight or branched chain alkyl group having from 1 to 20 carbon atoms.

Yet another group of penetration enhancers that can be used in the present invention are 1-substituted azacyclopentan-2-ones, as described in more detail in U.S. Pat. No. 4,444,762 to Jajadhyaksha, which patent is hereby incorporated by reference. These compounds have the structural formula:

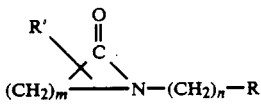

wherein R' is H or a lower alkyl group;
m is from 3 to 7;
n is from 0-17; and
R is —$CH_3$, phenyl, substituted phenyl, or

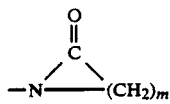

with the proviso that if m is 3 and R is —$CH_3$, then n is not from 0 to 6. These compounds can be used either alone or with $C_3$-$C_5$ diols.

Amides of the formula

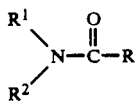

wherein $R^1$ and $R^2$ are independently selected from the group consisting of alkyl radicals and cycloalkyl radicals comprising from 1 to 20 carbon atoms and R is selected from the group consisting of alkyl radicals and cycloalkyl radicals comprising from 1 to 30 carbon atoms, and the total number of carbon atoms in the compound is at least 15. These compounds are described more fully in U.S. Pat. No. 4,808,414, to Peck et al., which patent is hereby incorporated by reference.

Sugar esters on combination with a sulfoxide or phosphine oxide can also be used to enhance penetration of the active ingredients. These sugar esters include hydrocarbyl and alkyl polyoxyalkylene esters of cyclic polyhydroxy saccharides wherein at least one of the hydroxyl groups on the saccharide moiety is substituted with an acyl or polyoxyalkylene group. These compounds are described in more detail in U.S. Pat. No. 3,896,238, to Smith, which patent is incorporated herein by reference.

The compositions of the present invention may be formulated into highly convenient dosage forms with thickening agents, including thickened solutions or lotions, ointments (including creams and gels), and the like.

Thickened solutions or lotions and ointments may be formed by incorporating with the penetration enhancer and the active ingredients, various gelling agents or other thickeners (viscosity increasers) which permit release of the active ingredients to the skin upon application. These forms are advantageously employed to lessen the runoff from the skin that may occur with the more fluid composition forms. Importantly, they also permit more sustained contact of the penetration enhancer with the treated surfaces, thus enhancing the speed of delivery of the active ingredients subcutaneously, and providing more accurate and controllable dosing. Accidental spilling and undesired contact with the material can also be minimized with these types of formulations.

It is advantageous to use water-dispersible thickening agents (i.e., agents dispersible in water to form a homogeneous distribution or solution), such as the polyethylene glycols, as they are readily compatible with water or other diluents to be formulated in the compositions, and they may be readily washed from the skin following absorption into the skin of the active ingredients. Alternatively, an emulsion base may be used to impart the desired thickening effect, together with the emollient effect of the lipoid phase of the emulsion base, a better spreading and wetting effect and a retardation of any skin-drying effect of the penetration enhancing compounds. When compositions are formulated with an emulsion base, the penetration enhancer is incorporated in the water phase thereof. Another category of thickening base which can also impart an emollient effect is provided by lipoidal thickening agents which are soluble in the penetration enhancer.

The water-soluble thickening bases may use polyethylene glycols of different viscosities, depending upon the desired consistency and concentration of penetration enhancer and vasodilator and vasoconstrictor to be incorporated in the compositions. Other thickening agents include water-dispersible gums, carboxyvinyl polymers, methyl cellulose, sodium carboxymethyl cellulose, alginates, and the like.

Lotions and ointments incorporating emulsion bases may contain the usual ingredients to provide the base, including fatty alcohols such as acetyl alcohol, an emulsifier such as lauryl sulfate, and water.

Pourable pharmaceutical dosages may be provided and dispensed in graduated containers, or containers which contain a given volume, such as 5 cc or the like. Containers with columns of 20 cc and above provide convenient multiple dosage forms, and those containing a typical single dose, such as from about 05.g to about 10 grams of a combination of vasodilator, vasoconstrictor, and penetration enhancer, provide convenient dosage forms. Squeeze tubes for lotions and ointments and cotton stick applicators may all be used for topical application of the thickened compositions.

The compositions of the present invention can also be administered by spraying and misting such as from misting devices and aerosol bottles, which containers are charged with fluid formulations containing at least 10% by weight of a combination of penetration enhancer, vasodilator, and vasoconstrictor, along with an aqueous diluent and, optionally, thickening agents, physiological salts, and the like. These compositions can be administered as either liquids or semisolid gels or mousses, depending upon the amount of gelling agents or surfactants included in the compositions. Compositions for this purpose are sufficiently fluid to permit dispensing by spray or mist from the container, and also meet the previously described criteria for penetrability and avoidance of undue side effects.

The following nonlimiting examples illustrate the compositions and dosage forms of this invention, and techniques for their preparation:

EXAMPLE 1

A liquid formulation is made from 750 mg nitroglycerine, 750 mg caffeine, 500 mg hydrocortisone, and 50 ml of dimethylsulfoxide in 40 ml distilled water. This composition may be applied topically in amounts of 0.1 to 5 g per application, generally by use of a cotton-tipped applicator.

EXAMPLE 2

An ointment is formulated from the following ingredients:

| | |
|---|---|
| nitroglycerin | 500 mg |
| caffeine | 250 mg |
| stearic acid | 40 g |
| acetyl alcohol | 5 g |
| triethanolamine | 4.2 g |
| glyceryl monostearate | 4.2 g |
| water | 40 ml |
| dimethylsulfoxide | 80 ml |

EXAMPLE 3

A spray composition according to the present invention is formulated as follows:

A 50% dimethylsulfoxide solution in isotonic saline is transferred to a 50 cc resilient plastic bottle, and 500 mg of nitroglycerine, 750 mg of caffeine, and 500 mg of hydrocortisone are added to the solution. A closure with a spray orifice is affixed to the bottle, from which the composition can be sprayed for topical administration.

EXAMPLE 4

A propellant spray composition is compounded from 50 ml water, 50 ml dimethyl sulfoxide, 1.5 nitroglycerin, glycerin, 1.5 g caffeine, 500 mg hydrocortisone, and a sufficient amount of propellent to provide a propellant force.

EXAMPLE 5

An ointment is prepared from the following ingredients:

| | |
|---|---|
| papaverine | 400 mg |
| epinephrine | 400 mg |
| stearic acid | 30 g |
| triethanolamine | 4 g |
| glyceryl monostearate | 4 g |
| water | 80 ml |
| dimethylsulfoxide | 80 ml |

EXAMPLE 6

A lotion formulation is prepared from the following ingredients:

| | |
|---|---|
| niocotinyl alcohol | 500 mg |
| caffeine | 500 mg |
| propylene glycol | 80 ml |
| glycerin | 20 ml |
| water | 10 ml |

EXAMPLE 7

A liquid preparation for treating impotence by topical application thereof is formulated from the following ingredients:

| | |
|---|---|
| isoxsuprine hydrochloride | 300 mg |
| caffeine | 300 mg |
| polyoxyethylene-2-sorbitan monolaurate | 60 ml |
| distilled water | 50 ml |
| hydrocortisone | 300 mg |

To treat impotence, the composition of the present invention is topically applied to the penis to cause an erection. Generally, amounts ranging from about 0.1 gram to about 5 grams of the composition are sufficient to be effective, although the determination of the effective amounts is well within the skill of the art.

Use of the subject invention in alleviating the problems of impotence is far superior to most other methods since it is substantially unobtrusive and is something of which the female sex partner need not be aware. Since this method of treatment provides vasodilation without treatment of the nervous aspect of inducing an erection, and includes vasoconstriction to retain the blood in the proper area, the erection may be sustained for a substantial period of time. In contrast, treatment involving devices to produce local stimulation, thereby inducing an erection, will sustain the erection for only a short period of time, since the nervous fibers are fatigued after a short time.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A composition for treating impotence consisting essentially of an effective amount of nitroglycerine as a vasocilator and an effective amount of caffeine as a vasoconstrictor, and a penetration enhancer, in a pharmaceutically acceptable carrier.

2. The composition according to claim 1 wherien said penetration enhancer is dimethylsulfoxide.

* * * * *